United States Patent
Srivastava et al.

(10) Patent No.: US 8,778,996 B2
(45) Date of Patent: Jul. 15, 2014

(54) METHOD OF TREATING A HUMAN BEING FOR A CLASS OF NEUROLOGICAL DEFECTS AND SEIZURE DISORDERS

(75) Inventors: Suresh C. Srivastava, Burlington, MA (US); Sant K. Srivastav, Burlington, MA (US); Stanley J. Szymanski, Jr., Sewickley, PA (US)

(73) Assignees: ChemGenes Corporation, Wilmington, MA (US); Stanley J. Szymanski, Jr., Sewickley, PA (US)

( * ) Notice: Subject to any disclaimer, the term of this patent is extended or adjusted under 35 U.S.C. 154(b) by 370 days.

(21) Appl. No.: 12/932,938

(22) Filed: Mar. 9, 2011

(65) Prior Publication Data

US 2011/0166230 A1 Jul. 7, 2011

Related U.S. Application Data

(62) Division of application No. 11/105,165, filed on Apr. 13, 2005, now Pat. No. 7,932,287.

(60) Provisional application No. 60/601,095, filed on Aug. 12, 2004.

(51) Int. Cl.
*A61K 31/195* (2006.01)

(52) U.S. Cl.
USPC .......................................................... 514/561

(58) Field of Classification Search
USPC .......................................................... 514/561
See application file for complete search history.

(56) References Cited

FOREIGN PATENT DOCUMENTS

GB 2006207 A * 5/1979

OTHER PUBLICATIONS

Beers et al., The Merck Manual of Medical Information, 2nd Edition, p. 496 (2003).*

* cited by examiner

*Primary Examiner* — Kevin E Weddington
(74) *Attorney, Agent, or Firm* — Law Offices of Indu M. Anand; Indu M. Anand, Esq.

(57) ABSTRACT

The invention involves various embodiments of a method for treating a human being for a condition associated with (1) seizures, myoclonic seizures, epilepsy, refractory epilepsy, hyperkinetic movements or tremors of hands or feet, (2) a state of ataxia, (3) accumulation of neuronal autofluorescent storage bodies in lysosomes or neurons, or regression of motor development, and (4) low alertness, dementia or mental retardation. The method involves administering a therapeutically effective salt of N-6-trimethyl-L-lysine.

2 Claims, No Drawings

METHOD OF TREATING A HUMAN BEING FOR A CLASS OF NEUROLOGICAL DEFECTS AND SEIZURE DISORDERS

CROSS-REFERENCE TO RELATED APPLICATIONS

This is a division of application Ser. No. 11/105,165, filed Apr. 13, 2005 now U.S. Pat. No. 7,932,287, which claims priority from provisional application No. 60/601,095 filed on Aug. 12, 2004, and incorporates the subject matter identified as Invention I, IX, XII, and XII in the Requirement for Restriction/Election of Jul. 25, 2008 in the parent application. All material referenced in the prior provisional and non-provisional applications are hereby incorporated by reference. This includes, but is not limited to, all specifications, drawings, and like materials.

Related divisional applications claiming similar priority include "Method of Synthesis and Purification of N-6-Trimethyl-L-Lysine and Derivative Compounds,"application Ser. No. 12/932,937; "Derivative Compounds of N-6-Trimethyl-L-Lysine for Therapeutic Use," application ser. No. 12/932,940; and "Method of Treating Human Being for a Class of Metabolic Defects and Energy Production Disorders," application Ser. No. 12/932,939.

All books, manuals, articles, and papers that are cited herein are hereby incorporated by reference in their entirety.

BACKGROUND OF THE INVENTION

1. Field of Invention

This invention relates to treatment of human beings for conditions associated with deficiencies in the N-6-trimethyl-L-lysine (TML) pathway affecting biosynthesis of carnitine. Such conditions include: (1) seizures, myoclonic seizures, epilepsy, refractory epilepsy, hyperkinetic movements, or tremors of the hands or feet, (2) a state of ataxia, (3) accumulation of neuronal autofluorescent storage bodies in lysosomes or neurons, or regression of motor development, and (4) low alertness, dementia, or mental retardation.

2. Description of Related Art

All material referenced in the prior provisional and non-provisional applications are hereby incorporated by reference.

Batten disease is named after the British pediatrician who first described it in 1903. It is also known as Spielmeyer-Vogt-Sjogren-Batten disease. The disease progresses and strikes without warning. The first signs of Batten Disease may be visual impairment and seizures. As the disease progresses, visual impairment leads to blindness and myoclonic seizures become more frequent and intense. A child with Batten Disease will also have a marked decline in cognitive function, noticeable personality and behavioral changes, a loss of communication skills, a loss of motor skills, apparent plasticity, facial grimacing and abnormal body movements. Thus Batten Disease leads to a vegetative state and is ultimately fatal (NINDS Batten Disease Information Page at http://www.ninds.nih.gov/disorders/batten/batten.htm, found in the parent application in Appendix A).

The parent application described the symptoms and common as well as distinct characteristics of the spectrum of NCL group, including the following: Batten Disease, Santavuori disease, Late-Infantile Neuronal Ceroid Lipofuscinoses (LINCL), Speilmeyer-Sjogren disease, Kuf disease, Parry disease, Bernheimer-Seitelberger syndrome, Bielschowsky amaurotic idiocy, Bielschowsky disease, Jansky-Bielschowsky disease, Seitelberger disease, late infantile amaurotic idiocy, late infantile Batten disease, subacute late infantile neuronal ceroid-lipofuscinosis, Zeman-Dyken-Lake-Santavuori-Savukoski disease.

At the genetic level, the neuronal ceroid lipofuscinoses (NCL's) result from mutations in at least eight genes, and these mutations are responsible for causing the various expressions of the neurodegenerative diseases collectively identified as NCLs. A summary background of these mutations and a survey of the background reference literature were given in the parent application. See Table A by Gene Locus.

TABLE A

| | Neuronal Ceroid Lipofuscinosis - Summary of Symptoms | | | | | | | | | |
|---|---|---|---|---|---|---|---|---|---|---|
| SYMPTOMS | CLN1 | CLN2 | CLN3 | CLN4 | CLN5 | CLN6 | CLN7 | CLN8 | CLN9 | CLN10 |
| Dementia | Yes | Yes | Yes | Yes | Yes | Yes | | | | |
| Seizures | Yes | Yes | Yes | Yes | Yes | Yes | Yes | Yes | Yes | yes (hyperknetic movements, hand/feet tremors) |
| Progressive Visual Failure | Yes | Yes | Yes | Yes | Yes | Yes | Yes | No | Yes | newborn infant |
| Mental Retardation | Yes | Yes | Yes | Yes | Yes | | Yes | Yes | | Yes |
| Loss Of Speech | Yes | Yes | Yes | | Yes | | Yes | | Yes | yes |
| Regression of Motor Development | Yes | Yes | | | Yes | | Yes | | Yes | yes |
| Ataxia | Yes | Yes | | Yes | Yes | | Yes | | Yes | yes |
| Muscular Hypotonia/Dystonia | Yes | Yes | | Yes | Yes | | | | | yes |
| Microcephaly | Yes | | | | | | | | | |
| Optic Atrophy/Macular Degeneration | Yes | Yes | Yes | | Yes | | | | | |
| Retinitis Pigmentosa | | | | | | | | | | |
| Myoclonus | Yes | Yes | Yes | Yes | Yes | | Yes | No | | |
| Cerebellar Atrophy | Yes | Yes | Yes | Yes | | | | | | yes |
| Quadraparesis | | Yes | | | | | | | | |

TABLE A-continued

Neuronal Ceroid Lipofuscinosis - Summary of Symptoms

| SYMPTOMS | CLN1 | CLN2 | CLN3 | CLN4 | CLN5 | CLN6 | CLN7 | CLN8 | CLN9 | CLN10 |
|---|---|---|---|---|---|---|---|---|---|---|
| Refractory Epilepsy | | Yes | | | | | | | | |
| Behavioral Involvement (Anger Outburst, Physical Violence) | | Yes | Yes | | | | | | | |

CLN1 (Infantile)
CLN2 (Late Infantile)
CLN3 (Juvenile)
CLN4a (Kufs Disease)
CLN5 (Late Infantile, Finnish Variant)
CLN6 (Late Infantile, Variant, Included, Variable age at onset)
CLN7 Late Infantile; allele to Northern Epilepsy
CLN8
CLN8 (Northern Epilepsy Variant)
CLN9
CLN10 (Cathepsin D-Deficient, Congenit
Table A Notes:
1. According to Mole et al.. 2005, the clinical course of the NCL's include progressive dementia, seizures, and progressive visual failure (Full text available at http://www.springerlink.com/content/xu2406100j81034w/fulltext.pdf).
2. Obviously, a 'yes' means that the symptom is a characteristic of the disease. A 'NO' means that the OMIM synopsis from clearly stated that the specific symptom is NOT characteristic of that particular NCL. An empty space for a particular symptom does not necessarily preclude it from being part of the characteristics of that particular NCL; it was not mentioned specifically in the OMIM synopsis. For instance, CLN6 is an LINCL(CLN2) variant. It did not specificallymention Mental Retardation or Loss of Speech or Cerebellar Atrophy; but it would be hard to believe that Mental Retardation/Loss of Speech/Cerebellar would not be part of the continuum.
3. References:
CLN1 http://www.ncbi.nlm.nih.gov/entrez/dispomim.cgi?id=256730
CLN2 http://www.ncbi.nlm.nih.gov/entrez/dispomim.cgi?id=204500
CLN3 http://www.ncbi.nlm.nih.gov/entrez/dispomim.cgi?id=204200
CLN4a http://www.ncbi.nlm.nih.gov/entrez/dispomim.cgi?id=204300
CLN5 http://www.ncbi.nlm.nih.gov/entrez/dispomim.cgi?id=256731
CLN6 http://www.ncbi.nlm.nih.gov/entrez/dispomim.cgi?id=601780
CLN7 http://www.ncbi.nlm.nih.gov/entrez/dispomim.cgi?id=610951
CLN8 http://www.ncbi.nlm.nih.gov/entrez/dispomim.cgi?id=600143
CLN8 (northern epilepsy variant) http://www.ncbi.nlm.nih.gov/entrez/dispomim.cgi?id=610003
CLN9 http://www.ncbi.nlm.nih.gov/entrez/dispomim.cgi?id=609055
CLN10 http://www.ncbi.nlm.nih.gov/entrez/dispomim.cgi?id=610127

Neuronal ceroid-lipofuscinosis are a group of inherited progressive neurometabolic diseases, previously considered as several separate syndromic entities, with considerable variability in clinical, pathological manifestations, and genetic findings. All diseases in this group are characterized by abnormal storage of the autofluorescent proteolipopigments in neuronal and other formulas with an average incidence estimated at 1:5/100,000. Abnormal proteins occur in the lysosomes, due to defects in lysosomal proteases or related enzymes or in other words, defective lysosomal proteolysis. Abnormal accumulation of proteins in various tissuess is not only responsible for the Batten disease, but it is also well known that it is responsible for other well known disorders, such as Alzheimer's disease, Parkinson's disease, Lewy body dementia, Huntington disease. In all these diseases, including Batten disease, undegraded proteins cause loss of neuronal cells.

NCLs are also classified on the basis of specific gene association and genetic features of the disease, age of onset, clinical manifestations, and pathological changes. The common characteristics in all of these disorders is accumulation of autofluorescent storage material in all tissues, but more pronounced in central nervous system. They are listed sequentially.

Neuronal ceroid-lipofuscinosis type 1 (CLN-1) Synonyms: Hagberg-Santavuori disease, Haltia-Santavuori disease, Santavuori disease, and several other synonyms. It is characterized by rapid deterioration with psychomotor retardation, loss of speech, seizures, ataxia, blindness, hypotonia, microcephaly, and occasional convulsions. Mapped to chromosome 1p32. The gene is known to be responsible for the making of palmitoyl-protein thioesterase. It is transmitted as an autosomal recessive trait. J. Vesa, E. Hellsten, L. A. Verkruyse, L. A. Camp, J. Rapola, P. Santavuori, S. L. Hofmann, L. Peltonen, Nature 376, 584-587,1995, E. Hellsten, J. Vesa, V. M. Olkkonen, A. Jalanko, L. Peltonen, EMBO J., 15, 5240-5245, 1996.

Neuronal ceroid-lipofuscinosis type 2 (CLN-2) Synonyms: Bernheimer-Seitelberger syndrome, Bielschowsky amaurotic idiocy, Bielschowsky disease, Jansky-Bielschowsky disease, Seitelberger disease, late infantile amaurotic idiocy, late infantile Batten disease, late infantile neuronal lipofuscinosis (LINCL), subacute late infantile neuronal ceroid-lipofuscinosis. This is the second most common variant with a subacute course after onset in infancy or early childhood characterized by refractive epilepsy, mental regression, ataxia, visual loss, and progressive deterioration. Mapped to chromosome 11p15. The CLN-2, the classical late infantile neuronal ceroid lipofuscinosis has been associated with mutation in a lysosomal protein. D. E. Sleat, R. J. Donnelly, H. Lackland, C.-G. liu, I. Sohar, R. K. Pullarkat and P. Lobel, Science 277, 1802-1805, 1997.

Neuronal ceroid-lipofuscinosis type 3 (CLN-3) Synonyms: Batten syndrome (BTS) Batten-Mayou syndrome, Batten-Spielmeyer-Vogt disease, Spielmeyer-Sjogren syndrome, Spielmeyer-Vogt-Batten disease, Spielmeyer-Vogt-Sjogren disease, Stock-Spielmeyer-Vogt syndrome, Vogt-Spielmeyer disease, chronic juvenile neuronal ceroid-lipofuscinosis (JNCL), juvenile amaurotic family idiocy, juvenile amaurotic idiocy, juvenile Batten disease, juvenile cerebrorenal degeneration, juvenile neuronal lipofuscinosis (JNCL), juvenile onset neuronal ceroid-lipofuscinosis, and pigmentary retinal neuronal heredodegeneration. The most commonly occurring variant has a chronic course after juvenile onset with an estimated incidence of 1:25,000. The first symptom is usually visual failure, which takes place between the ages of 4 and 15 years. The early symptoms are followed by epilepsy and progressive physical and mental deterioration. Batten disease gene maps to chromosome 16p12.1.56. Further it has been shown that the Batten disease protein CLN3P localizes into membrane lipid raits, which are detergent-resistant membranes (Rakheja D., Narayan S. B., Pastor J. V., Bennett M. J., Biochemical & Biophysical Research Communications. 317(4):988-991, 2004. Studies have been carried out on the intracellular trafficking of CLN3 protein, underlying the childhood neurodegenerative conditions of Batten disease (Mao Q., Xia H., Davidson B. L., FEBS Letters. 555(2):351-7, 2003).

Neuronal ceroid-lipofuscinosis type 4 (CLN-4) Synonyms: Kufs disease, Kufs-Mayer disease, adult amaurotic idiocy, adult ceroid lipofuscinosis, adult ganglioside lipidosis, adult neuronal ceroid-lipofuscinosis, adult recessive neuronal ceroid lipofuscinosis, chronic adult-recessive neuronal ceroid-lipofuscinosis, late familial amaurotic idiocy late ganglioside lipidosis. A rare variant with onset of symptoms between the ages of 20 and 50 years with a chronic course and associated with cerebellar ataxia, bulbar symptoms, and extrapyramidal and pyramidal signs, but without retinal lesions and rapidly progressive dementia. Transmitted as an autosomal recessive trait but some cases are sporadic. J.-J. Martin, Dev. Neurosci. 13, 331-338, 1991.

Neuronal ceroid-lipofuscinosis type 5 (CLN-5) Synonyms: Boehme disease, Parry neuronal ceroid-lipofuscinosis, adult dominant neuronal ceroid-lipofuscinosis, chronic adult dominant neuronal ceroid-lipofuscinosis, dominant Kufs disease, and dominant neuronal ceroid-lipofuscinosis. It is a cerebellar syndrome with onset early in the fourth decade, characterized by epileptic fits, myoclonic epilepsy, progressive dementia, and hypertension. CLN5 has been shown to be a novel gene encoding a transmembrane protein which is mutated in Finnish variant of LINCL. M. Savukoski, T. Klockars, V. Holmberg, P. Santavuori, E. S. Lander, L. Peltonen, Nat. Genet. 19, 286-288,1998.

Neuronal ceroid-lipofuscinosis type 6 (CLN-6) Synonyms: Zeman-Dyken-Lake-Santavuori-Savukoski disease, and subacute transitional early juvenile neuronal ceroid-lipofuscinosis. A subacute variant with onset in late childhood or in early period with seizures, ataxia, retinal lesions, mental failure, and gradual neurological deterioration. Novel mutations in the CLN6 gene caused a variant, late infantile neuronal ceroid lipofuscinosis (Teixeira C. A., Espinola J., Huo L., Kohischutter J., Persaud Sawin D. A., Minassian B., Bessa C. J., Guimaraes, A., Stephan D. A., Sa Miranda M. C., MacDonald M. E., Ribeiro M. G., Boustany R. M., Human Mutation. 21(5):502-8, 2003). Fine mapping of bovine ceroid lipofuscinosis was confirmed by orthology with CLN6 (Broom M. F., Zhou C., European Journal of Paediatric Neurology. 5 Suppl A:33-5, 2001). Analysis of candidate genes in the CLN6 critical region was also carried out using in silico cloning (Sharp J. D., Wheeler R. B., Schultz R. A., Joslin J. M., Mole S. E., Williams R. E., Gardiner R. M., European Journal of Paediatric Neurology. 5 Suppl A: 29-31, 2001). The loci for classical and late infantile neuronal ceroid lipofuscinosia have been shown to map to chromosomes 11p15 and 15q21-23 (J. D. Sharp, R. B. Wheeler, M. Savukoski, I. E. Jarvela, I. Peltonen, R. M. Gardiner, R. E. Williams, Hum. Mol. Genet., 6,591-595, 1997.

The palmitoyl protein thioesterase-2 (PPT2) gene encodes a lysosomal thioesterase homologous to PPT1. It has been shown that PPT2 deficiency in mice causes an unusual form of neuronal ceroid lipofuscinosis with striking visceral manifestations. In the study cited above (P. Gupta et al., 2001) all PPT2-deficient mice displayed a neurodegenerative phenotype with spasticity and ataxia by 15 months. The bone marrow of such mice was infiltrated by brightly autofluorescent macrophages and multinucleated giant cells. PPT2 deficiency in mice manifests as a neurodegenerative disorder with visceral features. Although PPT2 deficiency has not been described in humans, manifestations would be predicted to include neurodegeneration with bone marrow histiocytosis, visceromegaly, brown pancreas, and linkage to chromosome 6p21.3 in affected families (P. Gupta, A. A. Sombo, J. M. Shelton, I. G. Wilkofsky, K. E. Wisniewski, J. A. Richardson, and S. L. Hofmann, P.N.A.S. USA., 100 (21): 12325-12330, 2003).

The first three Russian cases of classical late-infantile neuronal ceroid lipofuscinosis have been reported (Lavrov, A. Y., Ilyna, E. S., Zakharova, E. Y., Boukina, A. M., Tishkanina, S. V., European Journal of Paediatric Neurology. 6(3): 161-4, 2002). There are also several possible subtypes—protracted, atypical, and earlier or later onset, which have similar clinical symptoms and may become apparent at different ages and progress at different rates. Ultimately, all forms are fatal. In the US, the incidence of all four types may be as high as two or three per 100,000 births. Batten disease is a fatal, inherited disorder of the nervous system that begins in childhood. "Late infantile neuronal ceroid lipofuscinosis (LINCL) is an autonomic excessive neurodegenerative disease caused by mutations in the CLN2 gene (NINDS Batten Disease Information Page at http://www.ninds.nih.govidisorders/batten/batten.htm attached with the parent application as Appendix A).

CLN2 encodes a lysosomal protease that was later found to be identical with lysosomal tripeptidyl peptidase. The specificity of lysosomal tripeptidyl peptidase-1 was determined by its action on angiotensin-II analogues (Warburton M. J., Bernardini F., FEBS Letters, 500(3): 145-8, 2001). It has been shown that the enzyme Palmitoyl protein thioesterase (PPT) localizes into synaptosomes and synaptic vesicles in neurons, and its implications for infantile neuronal ceroid lipofuscinosis (INCL) have been postulated (Lehtovirta, M., Kyttala, A., Eskelinen, E. L., Hess, M., Heinonen, 0., Jalanko, A., Human Molecular Genetics. 10 (1):69-75, 2001). An excellent review on the selectivity and types of cell death in the neuronal ceroid lipofuscinoses has been written (Mitchison H. M., Lim M. J., Cooper J. D., Brain Pathology, 14 (1):86-96, 2004). It was shown that optic nerve degeneration takes place in a murine model of juvenile ceroid lipofuscinosis (Sappington R. M., Pearce D. A., Calkins D. J., Investigative Ophthalmology & Visual Science. 44(9):3725-31, 2003).

At the cellular level, LINCL is characterized by lysosomal accumulation of autoflourescent storage material whose major identifiable component is mitochondria ATP synthase subunit c (subunit c) in neurons and other cell types. Affected individuals usually develop normally until about age 3 years, at which point they exhibit symptoms such as ataxia and seizure. The disease is associated with progressive loss of neurons and photoreceptors, and, within several years (NINDS; Batten Disease Information Page.). LINCL patients become blind, mute, bedridden and demented. Currently, there is no effective treatment for the disease and death typically occurs between age 6 and 15. Early symptoms of this disorder usually appear between the ages of 2 and 4, when parents or physicians may notice a previously normal child who has begun to develop vision problems or seizures (NINDS Batten Disease Information Page). In some cases the early signs are subtle, taking the form of personality and behavior changes, slow learning, clumsiness, or stumbling. Over time, affected children suffer mental impairment, worsening seizures, and progressive loss of sight and motor skills. Eventually, children with Batten disease become blind, bedridden, and demented, and the disease subsequently becomes fatal (NINDS Batten Disease Information Page).

Role of L-Carnitine

From a biochemical standpoint, L-carnitine plays an essential role in energy metabolism. In fatty acid metabolism, it serves as shuttle between the mitochondrial membrane and the mitochondria inner-workings permitting breakdown of the long-chain carbon fragment.

The more important role of L-carnitine is in maintaining a balance between the concentrations of a compound called acyl CoA in the cell compartments. For sugar to be metabolized, they are sequentially degraded to smaller fragments until carbon dioxide is produced, and along the way energy is conserved. Acyl CoA is an important intermediate in transfer of energy. Accordingly, it is important that the concentration of Acyl CoA be regulated and this function falls on L-carnitine. The role of L-carnitine and L-carnitine supplementation during exercise in humans has been illustrated (Brass E. P., Hiatt W. R., J. Am. Coll. Nutr., 17(3):207-215, 1998).

It has also been shown that defects in fatty acid oxidation are a source of major morbidity, particularly among children. Fatty acid oxidation defects encompass a spectrum of clinical disorders, including recurrent hypoglycemic, hypoketotic encephalopathy or Reye-like syndrome in infancy with secondary seizures and potential developmental delay, progressive lipid storage myopathy, recurrent myoglobinuria, neuropathy, and progressive cardiomyopathy. (I. Tein, J Child Neurol. 2002 December; 17 Suppl 3:3 S57-82; discussion 3S82-3).

Supplementation or treatment of a number of these diseases/disorders with L-carnitine has had beneficial effects. For example, some researchers believe L-carnitine supplementation may complement other therapies for the treatment of AIDS. (Effect of L-carnitine on human immunodeficiency virus-1 infection-associated apoptosis; Moretti S., Alesse E., Di Marzio L., a pilot study. Blood, 91(10):3817-3824, 1998). According to the authors, the treatment of immunodeficiency virus type 1 infections, acquired immune deficiency syndrome (AIDS), may elicit or cause carnitine deficiency problems. Additionally, some epileptic patients may benefit from carnitine supplementation or treatment.

L-carnitine may be essential or "conditionally" essential for several groups of people including: normal infants, premature infants, and both children and adults suffering from a variety of genetic, infectious, and injury-related illnesses. For example, some cardiomyopathies, which afflict children, are due to metabolic errors or deficiencies. There is data that supports treatment of some myocardial dysfunctions with L-carnitine supplementation. (Winter, S., Jue, K., Prochazka J., Francis, P., Hamilton, W., Linn, L., Helton, E. (1995) J. Child Neurol. 10, Supple 2: S45-51.)

L-carnitine may also play an essential role in the treatment of several disease conditions. Administration of L-carnitine prevents acute ammonia toxicity and enhances the efficacy of ammonia elimination as urea and glutamine. In addition, the cytotoxic effects of ammonia, possibly arising from lipid peroxidation, are ameliorated by L-carnitine. These data indicate the feasibility of utilization of L-carnitine in the therapy of human hyperammonemic syndromes, both for reducing the levels of ammonia and preventing its toxic effects. (O'Connor J E, Adv Exp Med. Biol. 1990; 272:183-95).

L-carnitine deficiency can be defined as a decrease of intracellular L-carnitine, leading to an accumulation of acyl-CoA esters and an inhibition of acyl-transport via the mitochondrial inner membrane. This may cause disease by the following processes:

A. Inhibition of the mitochondrial oxidation of long-chain fatty acids during fasting causes heart or liver failure. The latter may cause encephalopathy by hypoketonaemia, hypoglycemia and hyper-ammonemia. It was shown that acetyl-L-carnitine fed to old rats partially restores mitochondrial function and ambulatory activity (Hagen T M, Ingersoll R. T, Wehr C. M, Proc. Natl. Acad. Sci. USA., 95(16): 9562-9566, 1998).

B. Increased acyl-CoA esters inhibit many enzymes and carriers. Long-chain acyl-CoA affects mitochondrial oxidative phosphorylation at the adenine nucleotide carrier, and also inhibits other mitochondrial enzymes such as glutamate dehydrogenase, L-carnitine acetyltransferase and NAD transhydrogenase. (Scholte H R, J Clin Chem Clin Biochem. May 1990; 28(5): 35)

C. Accumulation of triacylglycerols in organs increases stress susceptibility by an exaggerated response to hormonal stimuli (Iyer, R. N., Khan, A. A., Gupta, A., Vajifdar, B. U., Lokhandwala, Y. Y., J Assoc Physicians India, 8(11):1050-1052, 2000).

D. Effect of L-carnitine on exercise tolerance in chronic stable angina: a multicenter, double-blind, randomized, placebo controlled crossover study (Cherchi, A., Lai, C., Angelino, F., et al., Int. J. Clin. Pharmacol. Ther. Toxicol., 23(10): 569-572, 1985).

E. Decreased mitochondrial acetyl-export lowers acetylcholine synthesis in the nervous system.

Primary L-carnitine deficiency can be defined as a genetic defect in the transport or biosynthesis of L-carnitine. Until now, only defects at the level of L-carnitine transport have been discovered. The most severe form of primary L-carnitine deficiency is the consequence of a lesion of the L-carnitine transport protein in the brush border membrane of the renal tubules. This defect causes cardiomyopathy or hepatic encephalopathy usually in combination with skeletal myopathy. In a patient with cardiomyopathy and without myopathy, it was found that L-carnitine transport at the level of the small intestinal epithelial brush border was also inhibited. The patient was cured by L-carnitine supplementation. Muscle L-carnitine increased, but remained too low, suggesting that L-carnitine transport in muscle is also inhibited. L-carnitine transport in fibroblasts was normal, which disagrees with literature reports for similar patients. W. R. Treem, C. A. Stanley, D. N. Finegold, D. E. Hale, P. M. Coates, N. Engl. J. Med, 319, 1331-1336, 1988; G. Karpati, S. Carpenter, A. G. Engel, G. Watters, J., Allen, S. Rothman, G. Klassen, 0. A. Mamer, Neurology, 25, 16-24, 1975; B. O. Eriksson, S. Lindstedt, I. Nordin, Eur. J. Pediatr., 147, 662-663, 1988; H. R. Scholte, R. Rodrigues Periera, P. C. de Jonge, I. E. Luyt-Houwen, M. Verduin, J. D. Ross, J. Clin. Chem. Clin. Biochem. 28, 351-357, 1990; C. A. Stanley, S. DeLeeuw, P. M. Coates, C. Vianey-Liaud, P. Divry, J. P. Bonnefont, J. M. Saudubray, M. Haymond, F. K. Tretz, G. N. Breningstall, Ann. Neuro. 30, 709-716, 1991; Y. Wang, J. Ye, V. Ganapati, N. Longo, Proc. Natl. Acad. Sci. USA 96, 2356-23601999.

In summary, L-carnitine plays a critical role in enhancing fat metabolism. Reports attest to the fact that L-carnitine works by transporting fatty acids to be burned for fuel, increasing both energy supply and lean muscle mass. Most reports also indicate that unless an individual is deficient in L-carnitine, it is an unnecessary ergogenic aid. This contrasts with an apparent need in case of L-carnitine deficiency (e.g., in the case pursued by the inventors of Late Infantile Neuronal Ceroid Lipofuscinosis-one form of Batten Disease), of the correct operation of the endogenous production of L-carnitine. This need was corroborated in the observations of dogs with Batten Disease given exogenous L-Carnitine (Siakotos A. N., Hutchins G. D., Farlow M. R., Katz M. L., European Journal of Paediatric Neurology 5 Suppl A: 151-6, 2001) and those of the parents of the child who was afflicted with LINCL (discussed below).

ATP Dependence on Endogenous L-Carnitine

Optimal ATP production from either dietary or stored fatty acids is dependent on L-carnitine. L-carnitine has several roles, most of which involve conjugation of acyl residues to the b-hydroxyl group of the L-carnitine with subsequent translocation of this complex from one cellular compartment to another. Deficiencies in L-carnitine have been implicated in a number of diseases. For example, in CLN3, proteins have been found to cause modulation of the cell growth rates and apoptosis (Persaud-Sawin D. A., Van Dongen A., Boustany R. M., Human Molecular Genetics. II(18):2129-42, 2002). It has been shown that defects in lysosomal enzymes cause Neuronal Ceroid Lipofuscinoses (NCLs), CLN1 and CLN2. (Hofmann S. L., Atashband A., Cho S. K., Das A. K., Gupta P., Lu J. Y., Current Molecular Medicine. 2(5):423-37, 2002). It has been also shown that the conditions of Parkinson's disease are present when there is dysfunction in both striatal and nigral neurons and this dysfunction results in autosomal dominant adult neuronal ceroid lipofuscinosis (Nijssen, P. C., Brusse, E., Leyten, A. C., Martin, J. J., Teepen, J. L., Roos, R. A., Movement Disorders, 17(3):482-7, 2002). It has been shown that abnormal accumulation of specific proteins occurs in the neuronal ceroid lipofuscinosis/Batten disease. These conditions result due to defect in the lysosomal proteases and related enzymes. The phenomenon is commonly termed as lysosomal proteinoses. This abnormal accumulation of proteins in the lysosomes has been shown to be responsible for major diseases such as Alzheimer disease, alpha-synuclein in Parkinson's disease, Lewy body dementia (Gupta, P., Hofmann, S. L., Molecular Psychiatry. 7(5):434-6, 2002). An autoantibody inhibitory to glutamic acid decarboxylase in the neurodegenerative disorder, Batten disease has been reported (Chattopadhyay, S., Ito, M., Cooper, J. D., Brooks, A. I., Curran, T. M., Powers, J. M., Pearce, D. A., Human Molecular Genetics. 11(12): 1421-31, 2002). Mutations in different proteins result in similar diseases of neuronal ceroid lipofuscinoses (Weimer, J. M., Kriscenski-Perry, E., Elshatory, Y., Pearce, D. A., NeuroMolecular Medicine. 1(2): 111-24, 2002). Lysosomal localization of the neuronal ceroid lipofuscinosis CLN5 protein. (Isosomppi, J., Vesa, J., Jalanko, A., Peltonen, L., Human Molecular Genetics. 11(8): 885-91, 2002).

Carnitine Biosynthesis & Metabolism

N-6-Trimethyl-L-Lysine (TML)

The enzyme Tripeptidyl Peptidase 1 (TPP-1) is responsible for cleaving "protein bound N-6-trimethyl-L-lysine" with the resulting products of free TML and amino acids in normal people. However, in children who have Late-Infantile Neuronal Ceroid Lipofuscinoses (LINCL), the TPP-1 is defective and the "protein-bound TML" is not broken down (M. L. Kaz, Biochem. Biophy. Acta, 1317, 192-198, 1996). It therefore becomes the storage material in the lysosome. Eventually it builds up and then consequently "blows up" the lysosome, causing eventual massive neuronal damage in brain and eventually death (P. Gupta and S. L. Hofmann, Molecular Psychiatry, 7, 434-436, 2002).

It has been shown that there is specific accumulation of a hydrophobic protein, subunit c of ATP synthase, in lysosomes from the cells of patients with LINCL, and is caused by a defect in the CLN2 gene product, TPP-1. The data by the authors show that TPP-1 is involved in the initial degradation of subunit c in lysosomes and suggest that its absence leads directly to the lysosomal accumulation of subunit c (Ezaki, J., Takeda-Ezaki, M., Kominami, E., J Biochem (tokyo) September, 128(3), 509, 2000).

Lysosomal hydrolysis of these proteins results in the release of TML, which is the first metabolite of L-carnitine biosynthesis. Hepatic synthesis of carnitine takes place from protein-bound N-6-trimethyl-L-lysine. Lysosmal digestion of methyl-lysine labeled asialo-fetuin was carried out (LaBadie, J., Dunn, W. A. and Aronson Jr, N. N. Biochem. J. 160, 85-95,1976). L-carnitine biosynthesis has been studied, such as, from gamma-butyrobetaine and from exogenous protein-bound-6-N-trimethyl-L-lysine by perfused guinea pig liver. In this connection, the effect of ascorbate deficiency on the in situ activity of gamma-butyrobetaine hydroxylase was demonstrated (Dunn, W. A., Rettura, G., Seifter, E. and Englard, S., J. Biol. Chem. 259, 10764-10770, 1984).

TML to L-Carnitine Pathway

TML is first hydroxylated on its 3-position to form 3-hydroxy-N-6-trimethyl-L-lysine (HTML). The aldolytic cleavage of HTML with HTML Aldolase (HTMLA) yields trimethylaminobutyraldehyde (TMABA) and glycine. Dehydrogenation of TMABA by TMABA dehydrogenase (TMABA-DH) results in the formation of 4-N-trimethylaminobutyrate (butyrobetaine). In the last step, gamma-butyrobetaine is hydroxylated on the 3 position by gamma-butyrobetain deoxygenase (BBD; EC to yield L-carnitine (Frederic M. Vaz and Ronald J. A. Wanders, Biochem. J. 361, 417-429, 2000). Very little is known about HTMLA. It might be identical to serine and lycine hydroxymethyltransferase (SHMT) which catalyses the tetrahydrofolate-dependent interconversion of serine and glycine (Girgis, S., Nasrallah, I. M., Suh, J. R., Oppenheim, E., Zanetti, K. A., Mastri, M. G. and Stover, P. J., Gene 210, 315-324, 1998). Purification and characterization of cytosolic and mitochondrial serine hydroxymethyltrasferase from rat liver was carried out (Ogawa, H. and Fujioka, M. J. Biochem. (Tokyo) 90, 381-390, 1981). SHMT also catalyses the aldol cleavage of other beta-hydroxylamino acids in absence of tetrahydrofolate, including HTML (Girgis, S., Nasrallah, I. M., Suh, J. R., Oppenheim, E., Zanetti, K. A., Mastri, M. G. and Stover, P. J. Gene 210, 315-324, 1998). Synthesis of butyrobetaine and L-carnitine from protein bound TML is inhibited by 1-amino-D-proline, an antagonist of vitamin B6. This inhibitory effect of 1-amino-D-proline on the production of L-carnitine from exogenous protein-bound N-6-trimethyl-L-lysine by the perfused rat liver has been shown. (Dunn, W. A., Aronson Jr, N. N. and Englard, S., J. Biol. Chem. 257, 7948-7951, 1982).

It is well known from the biochemistry of the metabolic pathway of TML to HTML that certain cofactors; such as 2-oxoglutarate, $Fe^{2+}$, molecular oxygen and ascorbate, have to be present. Similarly in the subsequent steps of metabolic pathway from HTML to L-carnitine, the biochemically defined cofactors have to be present. The cofactors (2-oxoglutarate, $Fe^{2+}$, molecular oxygen, and ascorbate) have been established by a number of researchers during the enzymatic hydroxylation of TML. It is likely that other chemicals will work as cofactors as well. For example, DTT (dithiothreitol) has been used instead of ascorbic acid (which is required to keep $Fe^{2+}$ in reduced form), in test tube conditions. Besides the aforesaid cofactors, calcium ion was found to cause significant enhancement in the conversion of TML to HTML (D. S. Sachan, C. L. Hoppel, Biochem. J., 188, 529-534, 1980).

4-N-trimethylaminobutyraldehyde dehydrogenase (TMABA-DH) catalyzes the dehydrogenation of 4-N-trimethylamino butyraldehyde to butyrobetaine. TMABA-DH has an absolute requirement for $NAD^+$. In human tissues, the rate of TMABA dehydrogenation is highest in liver, substantial in kidney, but low in brain, heart and muscle (Rebouche, C. J. and Engel, A. G., Biochim. Biophys. Acta, 22-29, 1980). TMABA-DH has been purified from beef liver (Hulse, J. D. and Henderson, L. M., Fed. Proc. Fed. Am. Soc. Exp. Biol., 38, 676, 1979).

Gamma-butyrobetaine dioxygenase (BBD) catalyses the stereospecific hydroxylation of butyrobetaine to L-carnitine in mammalian studies. BBD activity was stimulated considerably by 2-oxoglutarate, and the enzyme requires molecular oxygen, $Fe^{2+}$ and ascorbate for activity. (Lindblad, B., Lindstedt, G. and Tofft, M., J. Am. Chem. Soc., 91, 4604-4606, 1969). BBD activity has been found to be localized in the cytosol.

Kakimoto and Akazawa were the first to identify TML in human urine. All methods to assay TML in either plasma, urine or tissue samples use the same sample work-up. The concentration of TML in plasma is relatively constant in both human and rat, ranging from 0.2 to 1.3 micromole. Plasma levels of TML have been shown to correlate with body mass. In humans, urinary TML concentration is proportional to that of creatine. Furthermore, TML is not reabsorbed by kidney in humans. (Davis, A. T., Ingalls, S. T. and Hoppel, C. L J. Chromatogr. 306, 79-87, 1984.). In humans, TML concentrations range between 2 to 8 micromole per mmole of creatine. (Kakimoto, Y. and Akazawa, S., J. Biol. Chem. 245, 5751-5758, 1970).

Butyrobetaine is the last step in the synthesis of L-carnitine. The level of butyrobetaine in urine is low (about 0.3 micromole/mmol creatinine) (F. M. Vaz, B. Melegh, J. Bene, D. Cuebas, D. A. Gage, A Bootsma, P. Vreken, A. H. van Gennip, L. L. Bieber and R. J. A. Wanders, unpublished work) compared with the concentration in plasma of 4.8 micromole (Sandor, A., Minkler, P. E., Ingalls, S. T. and Hoppel, C. L., Clin. Chim. Acta., 176, 17-27, 1988).

Factors in the Biosynthesis & Control of L-Carnitine and N-6-Trimethyl-L-Lysine

Major sources of L-carnitine in the human diet are meat, fish and dairy products. Omnivorous humans generally ingest 2-12 micromoles of L-carnitine per day per kg of body weight. This is more than the L-carnitine produced endogenously, which has been estimated to be 1.2 micromole per day per kg of body weight. In omnivorous humans, approximately 75% of body L-carnitine sources come from the diet and 25% come from de novo biosynthesis. Since L-carnitine is present primarily in foods of animal origin, strict vegetarians obtain <0.1 micromole per day per kg of body weight. Strict vegetarians obtain more than 90% of their L-carnitine through biosynthesis.

Two primary intermediates have been proposed as the factors which limit biosynthesis of L-carnitine via their availability. These two intermediaries are g-butyrobetaine and N-6-trimethyl-L-lysine. Studies have shown that increasing the amount of either of these two intermediates in the bloodstream will increase the production of L-carnitine 100-fold in rats and 3-fold in human infants and adults (Olson and Rebouche, J. Nutr. 117(6), 1024-31,1987). Thus, L-carnitine biosynthesis may be regulated by one or all of the three enzymes which, together, catalyze the transformation of N-6-trimethyl-L-lysine into g-butyrobetaine. The high level of L-carnitine synthesis from exogenous L-carnitine precursors suggests that the enzymatic capacity to synthesize L-carnitine from TML and butyrobetain is much higher than is usually utilized. This suggests that only the availability of TML is the rate limiting step in the regulation of feedback inhibition for L-carnitine biosynthesis (Schematic 1). (F. M. Vaz and R. J. A. Wandars, Biochem. J., 361, 417-429, 2002).

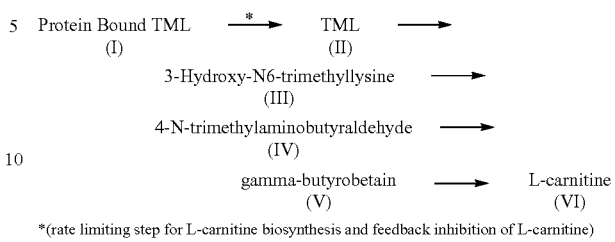

Schematic 1-Biosynthesis of L-Carnitine from TML (feedback regulation of TML)

Protein Bound TML —*→ TML ——→
(I) (II)
3-Hydroxy-N6-trimethyllysine ——→
(III)
4-N-trimethylaminobutyraldehyde ——→
(IV)
gamma-butyrobetain ——→ L-carnitine
(V) (VI)

*(rate limiting step for L-carnitine biosynthesis and feedback inhibition of L-carnitine)

L-ascorbic acid may be a principle co-factor in the metabolism of L-carnitine. It has been postulated and demonstrated that an experimental vitamin C deficiency resulted in increased urinary excretion of L-carnitine. This increased excretion of L-carnitine may be due to either decreased absorption from dietary sources, or increased excretion from the kidney. Several methods have been described to measure the concentration of L-carnitine biosynthesis metabolites in biological fluids and tissues.

The kidney plays a major role in L-carnitine biosynthesis, excretion and acylation. Unlike in the rat, the human kidney contains the enzymes needed to form L-carnitine from N-6 trimethyl-L-lysine (K, Doqi, National Kidney Foundation. Am. J. Kidney Dis., 35, 6 Suppl 2 S1-140, 2000). This L-carnitine precursor, TML, is found to be increased in plasma of patients with chronic renal failure. Free L-carnitine formed in the kidney as well as L-carnitine reabsorbed from the glomerular filtrate may be acylated in the proximal tubule. Isolated rat cortical tubule suspensions contain total L-carnitine concentrations of 2.85 micromols/g protein. During incubation over 60 min, the acylcarnitine/carnitine ratio decreased, indicating deacylation of acylcarnitine in proximal tubules. Exogenous L-carnitine was acylated at a rate of 35 micromols/h/g protein. Besides pyruvate and acetate, ketone bodies stimulated the acylation rate several fold, indicating that these substrates are a major source of acetyl-CoA for the acylation reaction. This may explain the higher acetylcarnitine/L-carnitine ratio found in urine under ketotic conditions.

However, later data shows that the brain also participates in active synthesis of L-carnitine from TML (F. M. Vaz and R. J. A. Wandars, Biochem. J., 361, 417-429, 2002). The concentration of butyrobetaine in plasma and tissues was determined by isolating butyrobetaine via HPLC or ion-exchange chromatography, and using BBD to convert it into L-carnitine. In humans, the level of butyrobetaine in urine is low (about 0.3 micromole/mmole L-creatinine) compared with the concentrations in plasma (4.8 mmole & 1.8 mmole).

The concentration of L-carnitine in plasma from both humans and rats is age and sex dependent. In humans, the plasma L-carnitine concentration increases during first year of life (from about 0.15 to about 0.40 mmole) and remains the same for both sexes until puberty. From puberty to adulthood, plasma L-carnitine concentrations in males increases and stabilizes at a level that is significantly higher than those in females (50 micromole compared to 40 micromole).

Obviously, carnitine is available from exogenous sources (meat, milk). However, work has been done to see if exogenous carnitine would ameliorate the symptoms of Juvenile Neuronal Ceroid Lipofuscinosis, not LINCL. This research in dogs showed that it made the dogs more functional and they lived 10% longer than untreated dogs, but the dogs still died very young compared to unaffected dogs and brain glucose hypometabolism and cerebral atrophy were not reduced (Siakotis, Katz et al., European Journal Pediatric Neurology 5, (Suppl. A): 151-156, 2001). It is an exciting prospect to see that TML may indeed be that therapeutic agent to cause positive brain metabolism based upon the results we have seen.

This invention provides a method of exogenic supplementation with TML to affect L-carnitine biosynthesis, thereby influencing ATP levels.

SUMMARY OF THE INVENTION

The present invention provides a method of administering a pharmaceutically acceptable salt of said N-6-trimethyl-L-lysine (TML) or derivative compound for treatment of conditions associated with a deficiency in the N-6-trimethyl-L-lysine pathway affecting biosynthesis of carnitine.

The modified TML derivatives described should have similar or near-similar results and improved biochemical properties. One of ordinary skill in the art would recognize that structural derivatives of TML, such as those mentioned in this application, may participate in the same biological processes and have the same and improved biochemical properties.

In one embodiment, the invention includes formulations or encapsulations of the compounds shown in Formulas I-VI for efficient intracellular delivery and as a prodrug of TML to proceed to make endogeneous L-carnitine, and to participate in various metabolic activities in the intermediate steps of L-carnitine biosynthesis pathway. These may be used for better adsorption of modified TML into various tissues such as kidney, liver and brain. The R', R", and aminoacyl groups are expected to hydrolyze inside the cellular media with one or more intracellular esterases to release free TML. Intracellular esterases are known to hydrolyze esters (Ghosh, M. and Mitra, A. K., Effects of 5'-Ester Modification on the Physicochemical Properties and Plasma Protein Binding of 5-Iodo-2'-Deoxyuridine. Pharm. Res., 8, 771-775, 1991).

It is believed that these can be used to treat a human being diagnosed with one or more of the following conditions: defects in carnitine biosynthesis pathway, efficiency of endogeneous TML, over-accumulation of TML bound protein at the cellular level, over-accumulation of glutamine in the brain, reduced and deficient fatty acid metabolism and shuttling of fatty acid in to mitochondria, insufficient ATP production or subsequent energy production and all the cellular activities associated with this events, defective fatty acid oxidation resulting from carnitine deficiency, hypoglycemia, hypoketotic, encephalopathy, reye-like syndrome, for recurrent seizures and developmental delay, over-accumulation of lipids causing myopathy, myoglobinuria, neuropathy, cardiomyopathy, ammonia over-production, hyperammonemic syndromes, over accumulation of triacylglycrols, Batten diseases, infantile neuronal lipofuscinoses diseases (Santavvori diseases), Late infantile neuronal lipofuscinoses diseases (Jansky-Bielscowsky), Speilmeyer disease, Sjorgsen disease, Kuf diseases, Parry diseases, juvenile or adult neuronal lipofuscinoses diseases ("NCL") disease, lysosomal accumulation of mitochondrial ATP synthase subunit and their by products, ataxia and seizures, various stages of mental impairment, (e.g., learning disability, clumsiness, stumbling, impaired motor skills, and dementia, hyperandrogenism caused by NCL, epileptic fits, and myoclonic epilepsy.

The invention utilizes compounds represented by Formulas I-VI (below) and having at least 98% purity; and preparations, prodrugs, formulations, and encapsulated forms thereof. CAS number for the TML compound is 23284-33-5.

The chemical structure of TML is commonly known to one of ordinary skill and the art and is represented by Formula 1 below:

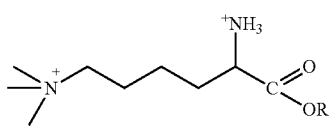

Formula 1

The TML derivatives are represented by the following Formulas II-VI:

Formula II:

Formula II wherein R' is selected from the group consisting of an alkyl having between 1 and 5 carbon atoms and an aromatic ring.

Formula III:

Formula III wherein R" is an alkyl having 1 to 5 carbon atoms or CH3.

Formula IV:

Formula IV wherein R" is an alkyl having between 1 and 5 carbon atoms, or CH3 and R' is an alkyl having between 1 and 5 carbon atoms or an aromatic ring.

Formula V:

(Formula V)

wherein a, a', b, b'; c, c', d, d', e, and e' are independently selected from H, deuterium, and an alkyl having between 1 and 5 carbon atoms; R' is selected from the group consisting of H, an alkyl having between 1 and 5 carbon atoms and an aromatic ring; and, and each N is independently selected from nitrogen and N15 labeled nitrogen.

Formula VI:

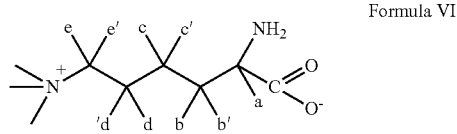

Formula VI wherein the a, b, b', c, c', d, d', e, and e' are independently selected from H, deuterium, and an alkyl having from 1 to 5 carbon atoms, and each N is independently selected from nitrogen and N15 labeled nitrogen.

DETAILED DESCRIPTION OF THE INVENTION

As used herein, the term "derivative" means any of Formulas II-VI. The invention incorporates both TML and TML derivatives. As such, any mention of TML also encapsulates the TML derivative compounds.

The phrase "pharmaceutically acceptable" indicates that the designated carrier, vehicle, diluent, excipient(s), and/or salt must be chemically and/or physically compatible with the other ingredients comprising the formulation, and physiologically compatible with the recipient thereof.

The term "prodrug" refers to a compound that is a drug or supplement precursor which, following administration, releases the drug or supplement in vivo via a chemical or physiological process (e.g., upon being brought to physiological pH or through enzyme activity). A discussion of the synthesis and use of prodrugs is provided by T. Higuchi and W. Stella, "Prodrugs as Novel Delivery Systems, Vol. 14 of the ACS Symposium Series, and in Biorevertible Carriers in Drug Design, ed. Edward B. Roche, American Pharmaceutical Association and Pergamon Press, 1987.

The term "treat" means to ameliorate or prevent at least one symptom of a disease or a condition.

As used herein, a "salt" can be an internal salt or an external salt. In internal salt, the carboxylic group (which is negatively charged) and the trimethyl group (which is positively charged) form an internal salt. The alpha amino group picks up the proton from the ionized carboxylic group when there is no external salt. In other embodiments, the proton from the ionized carboxylic group is picked up by one or more counterions (i.e., external molecule, atom, or group of atoms) thus forming the external salt. Sometimes, the counter ions can aggregate to include multiple ions. A typical example will be a molecule of water. These are generally multiple molecules and not a single molecule of water attached to a single ion.

Usually, the compound will include one or more different counterions (usually one for each of the two cationic sites in the molecules). The counter ions could be HO⁻, halides, sulfhydryl, carboxylic, phosphines, amines, organic anions, inorganic anions, or a mixture of organic and inorganic anions. These are well known to the skilled artisan. In some cases, there may only be one type of counter ion since internal zwitterions could leave only a single cationic site for salt formation.

One of ordinary skill in the art will further understand that the TML compound, Formula 1, is charged and thus has an internal salt or an external salt. External salts require one or more counterions. Hence, this compound may also include different counterions (usually one for each of the two cationic sites in the molecules). The counter ions could be HO⁻, halides, sulfhydryl, carboxylic, phosphines, amines, organic anions, inorganic anions, or a mixture of organic and inorganic anions, or other well known counterions In some cases, there may only be one type of counterion since internal zwitterions could leave only a single cationic site for salt formation. In yet another embodiment, there may be no counterions because there is an internal salt.

In another embodiment, the invention includes formulations or encapsulations of TML for efficient intracellular delivery and as a prodrug of TML to proceed to make endogeneous L-carnitine, and to participate in various metabolic activities in the intermediate steps of L-carnitine biosynthesis pathway. These may be used for better adsorption of modified TML into various tissues such as kidney, liver and brain.

TML is further provided in a physiologically acceptable carrier. These include various solvents, dispersion media, coatings, antibacterial and antifungal agents, isotonic and absorption delaying agents and like. The use of such media and agents for pharmaceutically active substances is well known in the art. Except, in so far as any conventional media or agent is incompatible with the active ingredient, its use in the therapeutic and supplement compositions is contemplated. Supplementary active ingredients can also be incorporated into the compositions.

These pharmaceutical and supplement formulations can be used to treat the afflicted diseases or disorders and conditions resulting from the TML deficiency and imbalance in the endogeneous L-carnitine biosynthesis pathway.

The method is to be in amount sufficient to exert the biochemical response and increase the conditions towards normalization.

The effective dosage of TML (or the pharmaceutically acceptable salt) and mode of administration in the treatment or improvement of conditions of various disorders can be determined by routine experimentation. The pharmaceutical or supplementation forms suitable for injectable use, or oral use, include sterile aqueous solutions or dispersions and sterile powders for the extemporaneous preparation of sterile injectable solutions or dispersions or oral formulations. In all cases the form must be sterile. It must be stable under the conditions of manufacture and storage and may be prepared against the contaminating effects and actions of microorganisms, such as bacterial and fungi. The carrier can be solvent or dispersion medium. The prevention of the action of microorganisms can be brought about by various antibacterial and antifungal agents. Prolonged absorption of the injectable or oral form can be brought about by the use of the compositions of agents delaying absorption.

TML (or the pharmaceutically acceptable salt) may be administered by any useful route including intravenous, intraperitoneal injection, intranasal, rectal, oral, transdermal or subcutaneous administration. Sterile injectable solutions are prepared by incorporating TML (or the pharmaceutically acceptable salt) in the required amount in the appropriate solvent, followed by sterilization.

TML (or the pharmaceutically acceptable salt) may be administered to a human being at dosage levels in the range of from about 0.1 mg to about 3,000 mg per day. For example, for a normal adult human having a body mass of about 70 kg, a dosage in the range of from about 0.01 mg to about 100 mg per kg body mass is typically sufficient. However, some variability in the general dosage range may be required depending upon the age and mass of the subject being treated, the intended route of administration, the particular compound being administered, and the like. The determination of dosage ranges and optimal dosages for a particular human subject is within the ability of one of ordinary skill in the art having benefit of the instant disclosure.

The pharmaceutical compositions of the invention may further comprise adjuvants, such as preserving, wetting, emulsifying, and dispersing agents. Prevention of microorganism contamination of the instant compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions may be affected by the use of agents capable of delaying absorption, for example, aluminum monostearate and gelatin.

Solid dosage forms for oral administration include capsules, tablets, powders, and granules. In such solid dosage forms, the active compound is admixed with at least one inert conventional pharmaceutical excipient (or carrier) such as sodium citrate or dicalcium phosphate, or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid certain complex silicates, and sodium carbonate; (e) solution retarders, as for example, paraffin; (f) absorption accelerators, as for example, quaternary ammonium compounds; (g) wetting agents, as for example, acetyl alcohol and glycerol monostearate; (h) adsorbents, as for example, kaolin and bentonite; and/or (i) lubricants, as for example, talc, calcium stearate, magnesium stearate, solid polyethylene glycols, sodium lauryl sulfate, or mixtures thereof. In the case of capsules and tablets, the dosage forms may further comprise buffering agents.

Solid compositions of a similar type may also be employed as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings and shells, such as enteric coatings and others well-known to one of ordinary skill in the art. They may also comprise opacifying agents, and can also be of such composition that they release the active compound in a delayed, sustained, or controlled manner. Examples of embedding compositions that can be employed are polymeric substances and waxes. The active compound can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the pharmaceutical composition can also include adjuvants, such as wetting agents, emulsifying and suspending agents, sweetening, flavoring, and perfuming agents.

Suspensions, in addition to the active compound, may further comprise suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by mixing an active compound with suitable non-irritating excipients or carriers such as cocoa butter, polyethylene glycol or a suppository wax, which are solid at ordinary room temperature, but liquid at body temperature, and therefore, melt in the rectum or vaginal cavity thereby releasing the active component.

Dosage forms for topical administration may comprise ointments, powders, sprays and inhalants. The active agent are admixed under sterile condition with a pharmaceutically acceptable carrier, vehicle, or diluent, and any preservatives, buffers, or propellants that may be required.

In one embodiment of the invention, the compounds of Formula I is administered to a human being along with supplementation for one or more co-factors required for carnitine biosynthesis. It is believed that the necessary co-factors are generally ingested through a normal diet or synthesized in vivo.

In another embodiment of the invention, any of the compounds of Formula I is administered to a human being along with supplementation for one or more co-factors required for the hydroxylation of N6-trimethyl-L-lysine by TML dioxygenase. These co-factors are: 2-oxoglutarate (alpha keto glutarate), $Fe^{2+}$, and ascorbate. Substitutes have also been found to be effective. For example, reducing agents such as dithiothreitol can take the place of ascorbate. (Vaz and Wanders, Biochem J. (2002) 361, 417-429). Molecular oxygen is also a co-factor, but is not required since a human being would breathe it in. Preferably, the one or more co-factors is given to the human being in an amount that is in excess of the molar equivalent of the TML or TML derivative administered to the human being. Calcium ion was found to cause significant enhancement in the conversion of TML to HTML (D. S. Sachan, C. L. Hoppel, Biochem. J., 188, 529-534, 1980). Thus, in a preferred embodiment, calcium ion supplementation is further administered to the human being, most preferably in an amount that is in excess of the molar equivalent of the given TML.

Experimental Study: Delivery of TML to a Child Diagnosed with Late Infantile Neuronal Ceroid Lipofuscinosis (LINCL) (Patient; Female, Age 6. Weight; 27 1 bs, Length: 36 Inches)

Child had been taking the supplements/vitamins listed in Appendix B (found in the parent application) for about three years before the start of TML therapy. In addition, she had been taking clonazepam (5-(2-chlorophenyl)-1,3-dihydro-7-nitro-2H-1,4-benzodiazepin-2-one) which is sold under the trade name Klonopin by F. Hoffmann-La Roche Ltd. (Basel, Switzerland) for control of constant Myoclonic seizures for about the same time according to the following daily dosage: (a) at waking: ½ of one 0.5 mg tablet, (b) Every four hours after waking, ¼ of one 0.5 mg tablet, (c) At bedtime: ½ of one 0.5 mg tablet. She also took one (1) 25 mg capsule of nitrofurantoin macrocrystals (sold under the name Macrodantin by Procter & Gamble Pharmaceuticals, Cincinnati Ohio) once per day.

"Baseline" blood work'was done after an overnight fast on the morning of Nov. 19, 2003. Child received her usual supplements/vitamins, clonazepam, and macrodantin. TML, as synthesized in Example 1 was given to the patient (5 mg of TML per day for a 30 day period, ending Dec. 28, 2003). Between Dec. 28, 2003 and Jan. 24, 2004, the child was given an alternating daily dose of 5 mg/day and 10 mg/day. On Jan.

24, 2004, and till the "new" blood work was done on Jan. 29, 2004, the patient received 10 mg/day by usually taking 5 mg of TML with breakfast and 5 mg of TML with dinner. She received 5 mg per dose during the duration of the experiment. In other words, she received TML once per day on days that she received 5 mg, and TML twice per day on days that she received 10 mg of TML. The TML was administered in powder form intermixed with her food.

Result after TML Therapy

The child's blood work results are in Table B, below, and the empirical nature of the child's improvement is evidenced by the follow up blood results. These blood tests were standard clinical tests carried out at Children's Hospital of Pittsburgh.

TABLE B

Results After TML Therapy.

| Test Name | Nov. 19, 2003 | Clinical Range | Jan. 29, 2004 | Clinical Range |
|---|---|---|---|---|
| Hgb | 14.4 | high | 14 | normal |
| HCT | 42 | high | 40.3 | normal |
| RDW | 11.5 | high | 12.3 | normal |
| ABS Lymphocytes | 2.2 | low | 2.5 | normal |
| Glycine | 50 | high | 25 | normal |
| Taurine | 24 | high | 19 | normal |
| Carnitine, Total | 40 | normal | 43 | normal |
| Carnitine, Esters | 7 | normal | 10 | normal |
| Alanine | 87 | high | 47 | normal |
| Carbon Dioxide | 32 | high | 22 | normal |
| BUN | 2 | low | 5 | (low) (6 is norm!) |
| AST | 60 | high | 50 (high) | (40 is norm) |
| Platelets | 586 | high | 461 (high) | (369 norm) |
| Glutamine | 99 | high | 70 | normal |

Notes to the Table B:
(a) CB = hemoglobin, HCT = Hematocrit, RDW Red Cell Distribution Width, ABS absolute, BUN Blood Urea Nitrogen, AST = Aspartate Amonotransferase)
(b) The examining physicians comments of Nov. 19, 2003 regarding Table B: (I) Alanine is elevated, this may be seen in states with increased pyruvate, (ii) Glutamine is increased, this may be seen, with Hyperammonemia.; Clinical correlation is indicated.
(c) The examining physicians comments on Jan. 29, 2004 that no significant elevation of serum amino acid was seen.
(d) The patient's glucose and potassium increased (Glucose 93 baseline to 132; Potassium 4.4 baseline to 4.8). Even though the follow up blood work was done after an all night fast, we did give her some "Gatorade" to drink before the blood test. This was given with her Klonopin to wash it down and certainly could be a contributing factor to the rise in glucose and potassium.

After Jan. 29, 2004, her parents continued giving her TML in varying doses (5 mg-30 mg) per day. The varying doses were based on the family's attempt to find an optimal dose. Her condition remained stable through January 2005.

Discussion of Experimental Study Results

Seizures, Myoclonic Seizures, Epilepsy, Refractory Epilepsy, Hyperkinetic Movements of the Hands or Feet Seizures (Myoclonic) began at approximately the age of 2 and ¾. Our patient's seizure and epilepsy status remarkably improved after the advent of her therapeutic intervention with TML. In the office visit to the physician (neurologist) Jan. 30, 2004, she told us that the patient looked healthy. Very importantly, the physician noted that the patient's myoclonic seizures were markedly reduced in severity and in number and that when the physician touched the patient, it no longer elicited a full body jerk (Myoclonus). She noted how calm the patient was. This is indeed VERY important as the guaranteed long-term clinical endgame for a child affected with LINCL is intractable, unstoppable seizures (no matter what kind of seizure medication or how high a dosage one gives) and death.

Epileptic patients may benefit from Carnitine supplementation. Supplementation or treatment of a number of these diseases/disorders with L-carnitine has had beneficial effects. For example, some researchers feel that L-carnitine supplementation may complement other therapies for the treatment of AIDS (Effect of L-carnitine on human immunodeficiency virus-1 infection-associated apoptosis; Moretti S., Alesse E., Di Marzio L., a pilot study. Blood, 91(10):3817-3824, 1998). According to the authors, the treatment of immunodeficiency virus type 1 infection/acquired immune deficiency syndrome (AIDS), may elicit or cause carnitine deficiency problems. Additionally, some epileptic patients may benefit from carnitine supplementation/treatment.

When you treat LINCL (Late Infantile Neuronal Ceroid Lipofuscinosis) or NCL (Neuronal Ceroid Lipofuscinosis) with TML or TML derivatives you are treating: Seizures (hyperkinetic movements & hand/feet tremors) and Myoclonus/Refractory Epilepsy or Epilepsy. This claim is borne out in the statements above that substantiate the improvement in the overall condition, including the status of the patient concerning her myoclonic seizures and indeed, the calmness of the patient.

In Table A (above), also included in the inventors originally published writing, we share the evidence that all forms of NCL have Seizures/hyperkinetic movements and hand and feet tremors common to their clinical synopsis. In addition, in the same Chart 2, 6 (six) out of 10 (ten) of the known forms of NCL have 'Myoclonus' common to their clinical synopsis. Finally, 'Refractory Epilepsy' is common to the clinical synopsis of CLN2.

Moreover, the official names of 2 forms of NCL identify the disease state with Epilepsy (this can be found above in Chart 3). The name of CLN7 is 'Late Infantile, allele to Northern Epilepsy.' The name of CLN8 is 'Progressive Epilepsy with mental retardation; Northern Epilepsy Variant.' It is not too much of a stretch to say that with the therapeutic intervention with TML is not only treating NCL, but in ameliorating the symptoms of NCL, the invention treats disease states (such as Seizures/hyperkinetic movements and hand and feet tremors; 'Myoclonus' 'Refractory Epilepsy' and 'Epilepsy') that are part of the description of the terrible clinical synopsis of the family of NCL's are recognized as 'stand alone' disease states on their own. Consequently, we hold that in the treating of defects in the N-6-Trimethyl-L-Lysine (TML) Pathway Affecting biosynthesis of Carnitine, the ability to positively treat, ameliorate and lessen: Seizures/hyperkinetic movements and hand and feet tremors; 'Myoclonus' 'Refractory Epilepsy' and 'Epilepsy' has been accomplished with the invention of the inventors.

Ataxia

Before TML therapy, the patient was physically "Dystonic." She was unable to hold herself up in a standing or sitting position. No meaningful control of arms, legs, feet or torso was seen. A small amount of head control was observed when she was held her mother or father in an upright position. She was very "hypertonic" in hands/fingers, arms, legs and ankles/feet.

After TML therapy her legs were still "hypertonic." However, a notable reduction in the hypertonicity of the child's arms, and hands and fingers was observed. This was also observed by a physiologist and neurologist.

'Ataxia' is common to 7 (seven) of the 10 (ten) forms of NCL. See Table A. The inventors assert that when a patient diagnosed with NCL is treated with TML that the symptoms that accompany condition are treated as well.

Accumulation of Neuronal Autofluorescent Storage Bodies in Brain and Lysosomes and Regression of Motor Development Above, the inventors set forth that the accumulation of autofluorescent proteolipopigments (autofluorescent storage bodies in neurons, neuron death) are common to all forms of NCL. Regression of motor development is common to 6 (six) out of the 10 (ten) forms of NCL. Since the protein accumulation (autofluorescent storage bodies in neurons, neuron death) are common to all forms of NCL, when one treats for NCL with the therapeutic intervention of TML, one treats the problem that is caused by the accumulation of said autofluorescent proteolipopigments (autofluorescent storage bodies in neurons, neuron death). When one treats NCL with therapeutic intervention of TML, the 'Regression of Motor Development' is treated as well.

Low Alertness, Dementia, and Mental Retardation

Before TML therapy, the child exhibited "Ptosis" of her eyelids (lids halfway down the eye) for much of the day and her general "alertness" was low.

After TML therapy, we observed more eye movement and even the emergence of "purposeful" eye movement and a faster pupillary response. If she was looking left, and somebody was standing on her right and asking her to look at the person, it took her a minute, but she began to regularly do it!

Also above, the inventors assert that 'Dementia' is common to 6 (six) of the 10 (ten) forms of NCL. 'Mental Retardation' is common to 8 (eight) of the 10 (ten) forms of NCL. When one treats a patient for NCL, the patient is also receives positive intervention into their conditions of 'Mental Retardation' and 'Dementia.'

We claim:

1. A method of treating a human being for a condition associated with a deficiency in the N-6-trimethyl-L-lysine (TML) pathway affecting biosynthesis of carnitine, by administration of a pharmaceutically acceptable salt of N-6-trimethyl-L-lysine (TML) or TML derivative, wherein said condition involves seizures, myoclonic seizures, epilepsy, refractory epilepsy, hyperkinetic movements or tremors of hands or feet.

2. The method of claim 1, wherein said pharmaceutically acceptable salt of N-6-trimethyl-L-lysine (TML) or TML derivative is of at least 98% purity.

* * * * *